United States Patent
Pauly

(10) Patent No.: US 11,783,950 B2
(45) Date of Patent: Oct. 10, 2023

(54) SYSTEM AND METHOD FOR PROVIDING A MEDICAL DATA STRUCTURE FOR A PATIENT

(71) Applicant: Siemens Healthcare GmbH, Erlangen (DE)

(72) Inventor: Olivier Pauly, Munich (DE)

(73) Assignee: Siemens Healthcare GmbH, Erlangen (DE)

(*) Notice: Subject to any disclaimer, the term of this patent is extended or adjusted under 35 U.S.C. 154(b) by 1119 days.

(21) Appl. No.: 16/514,108

(22) Filed: Jul. 17, 2019

(65) Prior Publication Data
US 2020/0035365 A1    Jan. 30, 2020

(30) Foreign Application Priority Data

Jul. 25, 2018 (EP) .................................... 18185493

(51) Int. Cl.
*G16H 50/70* (2018.01)
*G16H 15/00* (2018.01)
(Continued)

(52) U.S. Cl.
CPC .............. *G16H 50/70* (2018.01); *G06N 3/045* (2023.01); *G06N 3/08* (2013.01); *G16H 15/00* (2018.01);
(Continued)

(58) Field of Classification Search
CPC ........ G16H 50/70; G16H 15/00; G16H 50/20; G16H 10/20; G16H 10/40; G16H 10/60;
(Continued)

(56) References Cited

U.S. PATENT DOCUMENTS 5,687,716 A    11/1997 Kaufmann et al.
2015/0223759 A1    8/2015 Ong et al.
(Continued)

FOREIGN PATENT DOCUMENTS

EP    3223183 A1    9/2017

OTHER PUBLICATIONS

Lei, H., Wen, Y., You, Z., Elazab, A., Tan, E. L., Zhao, Y., & Lei, B. (2018). Protein-protein interactions prediction via multimodal deep polynomial network and regularized extreme learning machine. IEEE journal of biomedical and health informatics, 23(3), 1290-1303. (Year: 2018).*
(Continued)

*Primary Examiner* — Kamran Afshar
*Assistant Examiner* — Henry Trong Nguyen
(74) *Attorney, Agent, or Firm* — Harness, Dickey & Pierce, P.L.C.

(57) ABSTRACT

A method and a system are for providing a medical data structure for a patient. The system includes a plurality of data sources, each data source to provide medical data of the patient; a computing device to implement an artificial neural network structure a plurality of encoding modules, each being realized as an artificial neural network configured and trained to generate, from the medical data from the corresponding data source, a corresponding encoded output matrix; a weighting gate module for each of the encoding modules; a concatenation module configured to concatenate weighted output matrices of the weighting gates to a concatenated output matrix; and an aggregation module realized as an artificial neural network configured and trained to receive the concatenated output matrix and to generate therefrom the medical data structure for the patient, the artificial neural network structure being trained as a whole using a cost function.

24 Claims, 5 Drawing Sheets

(51) Int. Cl.
  G16H 50/20 (2018.01)
  G06N 3/08 (2023.01)
  G06N 3/045 (2023.01)
  G16H 50/50 (2018.01)
  G16H 10/40 (2018.01)
  G16H 10/60 (2018.01)
  G16H 70/40 (2018.01)
  G16H 10/20 (2018.01)
  G16H 70/20 (2018.01)

(52) U.S. Cl.
  CPC ............ *G16H 50/20* (2018.01); *G16H 10/20* (2018.01); *G16H 10/40* (2018.01); *G16H 10/60* (2018.01); *G16H 50/50* (2018.01); *G16H 70/20* (2018.01); *G16H 70/40* (2018.01)

(58) Field of Classification Search
  CPC ........ G16H 50/50; G16H 70/20; G16H 70/40; G16H 50/30; G06N 3/0454; G06N 3/08; H04L 67/1097
  See application file for complete search history.

(56) References Cited

U.S. PATENT DOCUMENTS

| | | |
|---|---|---|
| 2017/0293736 A1 | 10/2017 | Kramer et al. |
| 2018/0168516 A1 | 6/2018 | Pappada et al. |
| 2019/0139643 A1* | 5/2019 | Li .................. G06N 3/0454 |

OTHER PUBLICATIONS

Vu, T. D., Yang, H. J., Nguyen, V. Q., Oh, A. R., & Kim, M. S. (2017, February). Multimodal learning using convolution neural network and Sparse Autoencoder. In 2017 IEEE International Conference on Big Data and Smart Computing (BigComp) (pp. 309-312). IEEE. (Year: 2017).*

Lei et al., Protein-Protein Interactions Prediction via Multimodal Deep Polynomial Network and Regularized Extreme Learning Machine, Jun. 12, 2018, IEEE Journal of Biomedical and Health Informatics, 23(3), Europe PMC (https://europepmc.org/article/med/29994278), p. 1-13 (Year: 2018).*

Tsymbal, Alexey et al.: "Learning Discriminative Distance Functions for Case Retrieval and Decision Support"; Transactions on Case-Based Reasoning, vol. 3, No. 1, pp. 1-16; ISSN: 1867-366X; ISBN: 978-3-94-050117-2; XP055090974; 2010.

Hertz Homer et al., "Boosting Margin Based Distance Functions for Clustering", International Conference on Machine Learning; 2004.

Hinton, Geoffrey et al. "Discovering Binary Codes for Documents by Learning Deep Generative Models" Topics in Cognitive Science (2010), pp. 1-18; DOI: 10.1111/j.1756-8765.2010.01109.x; ISSN: 1756-8757 print /1756-8765 online; 2010.

Wikipedia: "Penalty method"; Anonymous; XP055547424.

Woznica Adam et al., Learning to Combine Distances for Complex Representations, Int. Conf. on Machine Learning; 2007.

Miotto, Riccardo et al., "Deep Patient: An Unsupervised Representation to Predict the Future of Patients from the Electronic Health Records", in: Nature Scientific Reports, vol. 6, No. 26094, 2016, DOI: 10.1038/srep26094.

Weinberger Kilian et al., "Distance metric learning for large margin nearest neighbor classification", The Journal of Machine Learning Research, 10, pp. 207-244; 2009.

Weinberger Kilian et al., "Distance Metric Learning for Large Margin Nearest Neighbor Classification", Int. Conf. on Neural Information Processing Systems; 2005.

Clinchant S et al., "Semantic Combination of Textual and Visual Information in Multimedia Retrieval", Int. Conf. on Multimedia Retrieval; 2011.

Wikipedia: "Artificial Neural Network"; XP055546856.

Bar-Hillel, Aharon et al., "Learning a Mahalanobis Metric from Equivalence Constraints", in: Journal of Machine Learning Research, vol. 6 No. 6, pp. 937-965, 2005.

Hastie Trevor et al., "Discriminant adaptive nearest neighbor classification", IEEE Transactions on Pattern Analysis and Machine Intelligence, 18(6), pp. 607-616; 1996.

NPL: European Search Report for EP Application Patent No. 18185493, dated Jan. 28, 2019.

* cited by examiner

SYSTEM AND METHOD FOR PROVIDING A MEDICAL DATA STRUCTURE FOR A PATIENT

PRIORITY STATEMENT

The present application hereby claims priority under 35 U.S.C. § 119 to European patent application number EP 18185493.6 filed Jul. 25, 2018, the entire contents of which are hereby incorporated herein by reference.

FIELD

Embodiments of the invention generally relate to the technical field of healthcare.

BACKGROUND

In the technical field of healthcare, mining large amounts of data is expected to lead to the discovery of new correlations, factors, biomarkers, or even new drugs to enhance treatments in the future.

Access to this data, however, remains difficult due to the sheer amount of data and the high-dimensional and multi-modal nature of the data. Multi-modal in this context means that data may be collected, expressed and stored in many different ways ("modes" or "modalities") which are sometimes difficult to bring into context with each other. Data sources may comprise imaging, laboratory test measurements, clinical and family history, and the like.

For example, some medical data, e.g. recent accidents of a patient, may be entered manually into a database (e.g.: "Current weight: xxx kg"). For the same patient, there may also be image data from magnetic resonance imaging (MRI). The weight of the patient at the time of the imaging may be correlated with an amount or structure of fat tissue in the MRI data so that, by combining information from both data sources (or: "modalities") conclusions may be made which exceed what may be deduced from either data source individually. However, due to the different formats of these data, finding and exploiting such links between modalities is challenging, especially on a large scale.

A main tool for providing improved diagnoses or predictions is finding similarities between the case of a patient to be diagnosed and cases of previous patients. Modelling similarity of cases using such disparate data types is further challenging due to, for example, wide differences in data dimensionality, differences in predictive information content within and/or between the various sources, and different scales or structures for different data types.

To leverage the large volume of potentially valuable data, similarity-search-based information retrieval may be used. Similarity-search-based information retrieval, however, suffers from not being scalable to large amounts of data (e.g., an amount of cases within the data and a number of features within a case) and is unable to process multi-modal data.

For example, a particular mode of data, such as imaging, may have 300 variables, while another mode of data has two variables. A classical distance measure employed to assess similarity may produce similarity scores that are dominated by the imaging data at the expense of the minority data source with two variables.

In an example where the minority data source is the presence or absence of a recent health event that is strongly predictive of an outcome (i.e. highly relevant for a task at hand), the minority data source is often not given enough weight when assessing similarity.

From EP 3 223 183 A1, systems and methods are known which encode original, multi-modal data into a medical data structure ("compact signature") of the patient. Advantageously, the compact signature has a smaller dimensionality than the totality of the medical data of the patient present in all of the different modalities. Moreover, a neural network configured to produce the compact signature may be trained such that equally important variables or facts are weighted essentially equally within the compact signature. Clinical outcomes may then be predicted based on similarities between the compact signatures of different patients, rather than on similarities between the data of the individual modalities.

Methods of producing more relevant data from large numbers of medical input data are also discussed in the scientific publication "Deep Patient: An Unsupervised Representation to Predict the Future of Patients from the Electronic Health Records", by Riccardo Miotto, Li Li, Brian A. Kidd and Joel T. Dudley, in: Nature Scientific Reports, volume 6, Article Number 26094, DOI:10.1038/srep26094, cited herein as "Miotto et al.".

It is also known to utilize cloud computing systems for processing medical data of patients.

In systems based on cloud computing technology, a large number of devices is connected to a cloud computing system via the Internet. The devices may be located in a facility, such as a hospital, connected to the cloud computing system. For example, the devices can comprise, or consist of, equipments, sensors, actuators, robots, and/or machinery in an industrial set-up. The devices can be medical devices and equipments in a healthcare unit. The devices can be home appliances or office appliances in a residential/commercial establishment.

The cloud computing system may enable remote configuring, monitoring, controlling, and maintaining connected devices (also commonly known as 'assets'). Also, the cloud computing system may facilitate storing large amounts of data periodically gathered from the devices, analyzing the large amounts of data, and providing insights (e.g., Key Performance Indicators, Outliers) and alerts to operators, field engineers or owners of the devices via a graphical user interface (e.g., of web applications). The insights and alerts may enable controlling and maintaining the devices, leading to efficient and fail-safe operation of the devices. The cloud computing system may also enable modifying parameters associated with the devices and issues control commands via the graphical user interface based on the insights and alerts.

The cloud computing system may comprise a plurality of servers or processors (also known as 'cloud infrastructure'), which are geographically distributed, connected with each other via a network. A dedicated platform is installed on the servers/processors for providing above functionality as a service. The cloud computing platform may comprise a plurality of software programs executed on one or more servers or processors of the cloud computing system to enable delivery of the requested service to the devices and its users.

One or more application programming interfaces (APIs) are deployed in the cloud computing system to deliver various cloud services to the users.

SUMMARY

At least one embodiment of the present invention provides improved methods and systems to generate medical data structures (which may also be designated as "compact signatures" or "digital medical fingerprints") for patients, to provide improved and extended applications for these structures and to present improved ways of training artificial neural networks.

Therefore, according to a first embodiment, the present invention provides a system for providing a medical data structure for a patient, comprising:

a plurality of data sources, each data source of the plurality of data sources being configured to provide medical data of the patient;

a computing device configured to implement an artificial neural network structure trained using a cost function, the artificial neural network structure including:

a plurality of encoding modules, at least one of the plurality of encoding modules being provided for each data source, each encoding module of the plurality of encoding modules being realized as an artificial neural network configured and trained to generate, from the medical data from a corresponding data source of the plurality of data sources, a corresponding encoded output matrix;

a plurality of weighting gate modules, one weighting gate module of the plurality of weighting gate modules being provided for each of the plurality of encoding modules, each one weighting gate module being configured to weight the encoded output matrix of a corresponding encoding module, of the plurality of encoding modules, by multiplying the corresponding encoding module with a corresponding weighting factor, to produce a corresponding weighted output matrix, to produce weighted output matrices;

a concatenation module configured to concatenate the weighted output matrices to a concatenated corresponding output matrix, to produce a concatenated output matrix; and an aggregation module, realized as an artificial neural network, configured and trained to receive the concatenated output matrix and to generate, from the concatenated output matrix, the medical data structure for the patient.

The invention further provides, according to a second embodiment, a method for providing a medical data structure for a patient, comprising:

providing medical data of the patient from a plurality of data sources;

providing a trained artificial neural network structure, the artificial neural network structure including a plurality of encoding modules, including at least one encoding module for each data source of the plurality of data sources;

generating, by the plurality of encoding modules, from corresponding medical data of each of corresponding data sources, a corresponding encoded output matrix, to produce encoded output matrices;

weighting the encoded output matrices by multiplying each of the encoded output matrices with a weighting factor, to produce weighted output matrices;

concatenating the weighted output matrices to a concatenated output matrix;

generating the medical data structure for the patient from the concatenated output matrix using an aggregation module realized as a trained artificial neural network.

According to a third embodiment, the invention provides a computer program product comprising executable program code configured to, when executed, perform the method according to the second embodiment.

According to a fourth embodiment, the invention provides a non-transient computer-readable data storage medium comprising executable program code configured to, when executed, perform the method according to the second embodiment.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, a USB memory stick or the like.

According to a fifth embodiment, the invention provides a data stream representing, or configured to provide, program code configured to, when executed, perform the method according to the second embodiment.

According to a sixth embodiment, the invention provides a method for training an artificial neuronal network structure, preferably as a whole, to generate the artificial neuronal network structure used in the system according to the first embodiment.

Further advantages and preferred embodiments will be evident from the claims as well as from the description, taking into account also the attached figures.

The invention will be explained in greater detail with reference to example embodiments depicted in the drawings as appended.

BRIEF DESCRIPTION OF THE DRAWINGS

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as they become better understood by reference to the following detailed description. Like reference numerals designate corresponding similar parts.

DETAILED DESCRIPTION OF THE EXAMPLE EMBODIMENTS

Figure 1:
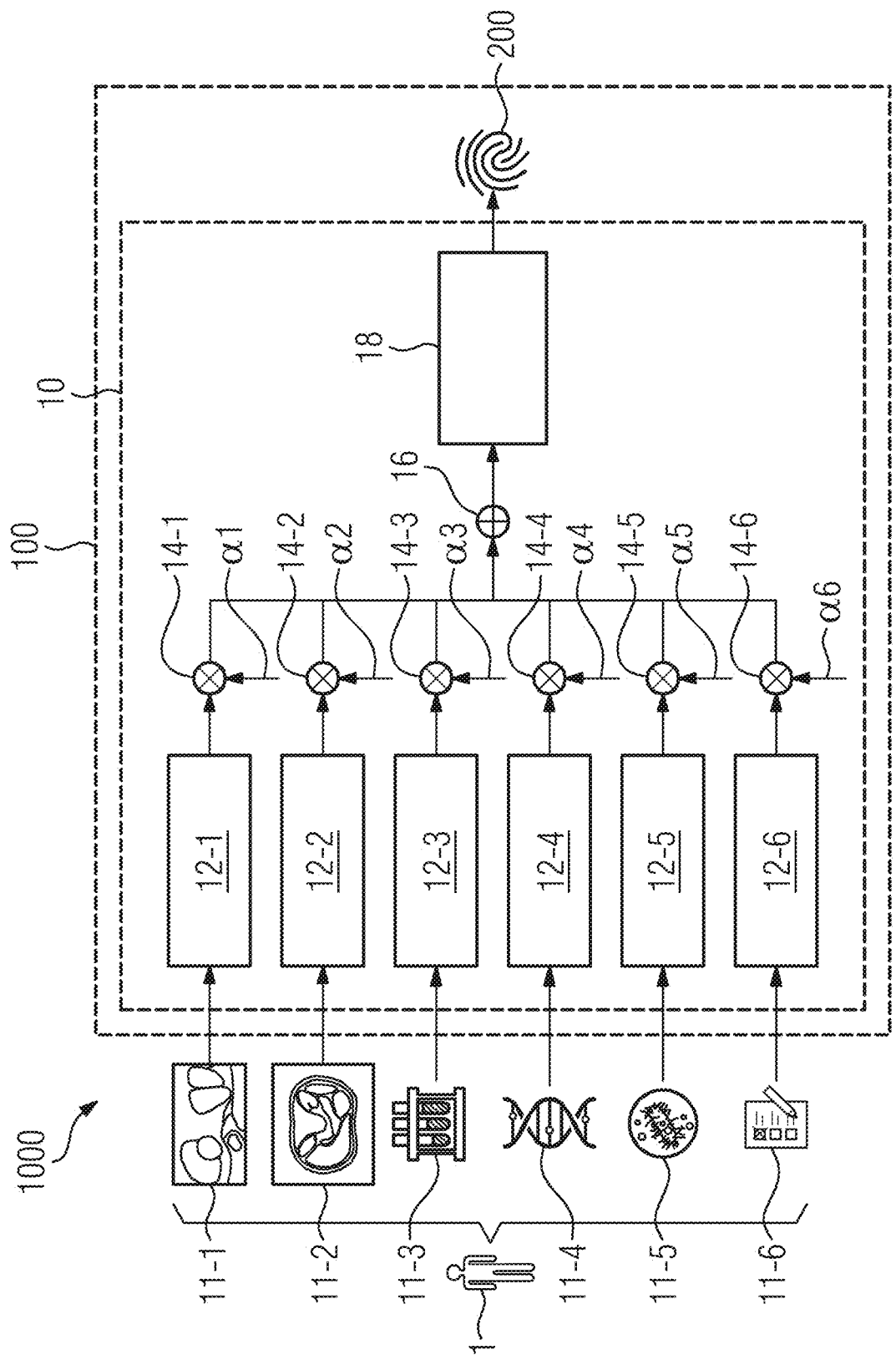
FIG. 1 shows a schematic diagram illustrating a system according to an embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Therefore, according to a first embodiment, the present invention provides a system for providing a medical data structure for a patient, comprising:
a plurality of data sources, each data source configured to provide medical data of the patient;
a computing device configured to implement an artificial neural network structure trained using a cost function E, the artificial neural network structure comprising:
a plurality of encoding modules, at least one for each data source, each encoding module being realized as an artificial neural network configured and trained to generate, from the medical data from the corresponding data source, a corresponding encoded output matrix;
a weighting gate module for each of the encoding modules, each weighting gate module configured to weight the encoded output matrix of the corresponding encoding module by multiplying it with a weighting factor;
a concatenation module configured to concatenate the weighted output matrices of the weighting gates to a concatenated output matrix; and
an aggregation module realized as an artificial neural network configured and trained to receive the concatenated output matrix and to generate therefrom the medical data structure for the patient.

Each data source may be any source that is capable of providing medical data of the patient. In particular, each data source may represent, or be connected to, a different data source (or: modality) of medical data of the patient.

Data sources may include:
ultrasound imaging data
PET (positron emission tomography) imaging data
MRI (magnetic resonance imaging) data
other imaging data
lab test result data (e.g. bloodwork)
genetic data
questionnaire data
and/or others.

Some or all of the data sources may be data interfaces that connect the system to external or internal data storage sections, wherein the data interfaces may be realized in hardware and/or software. For example, a first data interface may be a software interface adapted to access a database with patient data, a second data interface may comprise a data cable linking the computing device to an imaging device (such as an MRI device), a third data interface may be a software agent adapted to retrieve information about the patient from the internet and/or a remote data depository or a distributed data depository, and so on.

A computing device, as the term is used herein, should be understood to be any hardware device or processor for computing, i.e. for running a software or an algorithm. For example, the computing device may be a single processor core or a microprocessor. Preferably, the computing device comprises, or consists of, an array of processor cores or central processing units (CPUs). More preferably, the computing device comprises, or consists of, an array of graphical processing units (GPUs).

The computing device may be realized partially or completely by interconnected remote devices such as cloud computing servers and/or as a virtual machine.

A matrix, as used herein, may be understood in a broad mathematical sense as an array of m times n entries, wherein m is a positive integer denoting a number of lines of the matrix and n is a positive integer denoting a number of columns of the matrix. In other words, a vector with m entries may be seen as an "m times 1" matrix, and a scalar may be seen as a "1 times 1" matrix. In some embodiments, a matrix may however designate a matrix in a stricter sense, i.e. having at least two lines and at least two rows (i.e. $m>1$, $n>1$).

The encoded output matrices preferably have a dimension that is lower than the medical data from which they are generated. Specifically, the length of a vector representing medical data of the patient may be longer than the length of a vector that is an encoded output matrix encoded from the vector of medical data by an encoding module. In this way, irrelevant or redundant info may be faded out, reducing complexity as well as necessary computing power and electricity.

Weighting an encoded output matrix by a weighting factor should be understood as, for example, multiplying each entry of the output matrix by the weighting factor.

The weighting factors used by the weighting gate modules may be set manually by a user or, as a preferred alternative, may be learned during training of the artificial neural network structure. Preferably, the weighting factors have values between zero and one, both included. If a weighting factor is set to one, then the output of the corresponding data source (or: modality) is unchanged. If a weighting factor is set to zero, then the information from the corresponding data source is switched off, or ignored.

Such a switching off may, in some embodiments, be performed by leaving out the matrix (e.g. vector) produced by the corresponding encoding module from the subsequent concatenation. In preferred embodiments, however, the entries of the concatenated output matrix which would be formed by the weighted entries of the switch-off data source may simply be set to zero such that the dimensionality of the concatenated output matrix remains fixed at all times.

Preferably, the medical data structure (or: "compact signature") of the patient is provided in a task-specific way, i.e. as optimized for a specific diagnostic task and/or prediction task. The system may therefore be designated also a system for providing a task-specific medical data structure for a patient.

A diagnostic task may be e.g. to determine if, or with which probability, the patient has a certain disease. A prediction task may be e.g. to determine how much time will pass until a specific medical event happens with a predetermined likelihood, e.g. the patient passing from a first stage of a disease to a second stage, the patient developing a specific symptom, the patient being cured, or the like.

One advantage of the system according to the first embodiment is that, by providing the weighting gate modules, medical data structure may be made more task-specific, for example by setting comparatively small weighting factors for data sources (or: modalities) that are known to have a comparatively low influence on the task at hand, and setting comparatively large weighting factors for data sources that are known to have a comparatively high influence on the task at hand.

For example, when the task is to determine whether the patient has a certain pulmonary disease, information from a data source that provides imaging data of the patient's heart may be provided with a low weighting factor (e.g. smaller than ten percent of the available range of weighting factors) or may be switched off completely, whereas imaging data of the patient's lungs may be provided with a high weighting factor (e.g. larger than ninety percent of the available range of weighting factors).

The weighting factors $\alpha_i$ may be configured such that in sum they yield 1 ($\Sigma_i \alpha_i = 1$) such that, when a user increases one of the weighting factors, the other weighting factors are correspondingly lowered and vice versa.

During training, parameters $\theta$ of the artificial neuronal network structure are optimized with respect to the cost function (or: "loss function"), based on labelled training data. Parameters $\theta$ may include in particular weights and biases of connections and nodes of the artificial neuronal networks in the artificial neuronal network structure.

Preferably, the artificial neural network structure is (i.e. has been) trained as a whole, or, in other words, all trainable elements of the artificial neural network structure are preferably trained simultaneously.

The invention further provides, according to a second embodiment, a method for providing a medical data structure for a patient, comprising:
  providing medical data of the patient from a plurality of data sources;
  providing a trained artificial neural network structure, the artificial neural network structure comprising at least one encoding module for each data source;
  generating, by the encoding modules, from the corresponding medical data of the corresponding data source, a corresponding encoded output matrix;
  weighting the encoded output matrices of the encoding modules by multiplying each with a weighting factor;
  concatenating the weighted output matrices of the weighting gates to a concatenated output matrix; and
  generating the medical data structure for the patient from the concatenated output matrix using an aggregation module realized as a trained artificial neural network.

Providing the trained artificial neural network structure preferably comprises training the artificial neural network structure using a cost function, in particular training the artificial neural network structure as a whole using the cost function.

According to third embodiment, the invention provides a computer program product comprising executable program code configured to, when executed, perform the method according to the second embodiment.

According to a fourth embodiment, the invention provides a non-transient computer-readable data storage medium comprising executable program code configured to, when executed, perform the method according to the second embodiment.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, a USB memory stick or the like.

According to a fifth embodiment, the invention provides a data stream representing, or configured to provide, program code configured to, when executed, perform the method according to the second embodiment.

According to a sixth embodiment, the invention provides a method for training an artificial neuronal network structure, preferably as a whole, to generate the artificial neuronal network structure used in the system according to the first embodiment.

Further advantages and preferred embodiments will be evident from the claims as well as from the description, taking into account also the attached figures.

In some advantageous embodiments, the weighting factors of the weighting gate modules are learned during training with the cost function. In other words, the weighting factors may be treated as parameters of the artificial neuronal network structure (instead of, for example, as fixed hyperparameters). In this way, the weighting factors are further optimized. This is particularly useful when combined with the options for training the artificial neural network structure as described in the following.

In some advantageous embodiments, the artificial neural network structure comprises a task-specific artificial neural network (or: "task-specific sub-network") configured and trained to perform, using the medical data structure as an input, a diagnostic and/or prediction task for the patient. A so-called task output matrix indicating a result of the diagnostic and/or prediction task may be output by the task-specific artificial neural network. The task output matrix may be a single number with a discrete target set, in particular a binary target set, e.g. one and zero (representing e.g. "risk present" and "risk absent", respectively, or "risk above threshold x %" and "risk below threshold x %", respectively).

The cost function used for training the artificial neural network structure with training data may be designed such that it penalizes differences between the task output matrices for the training data and corresponding labels of the training data.

In some advantageous embodiments, the artificial neural network structure comprises a domain-specific artificial neural network (or: "domain-specific sub-network") configured and trained to determine, using the medical data structure as an input, a medical domain for the patient and for the diagnostic and/or prediction task and to output a domain output matrix indicating the determined medical domain.

The cost function used for training the artificial neural network structure may comprise a term that penalizes differences between the domain output matrices for the training data and corresponding labels of the training data.

The domain-specific artificial neural network may be used to bias the training such that known relationships are maintained and observed by the trained artificial neural network structure. The domain may, for example, be a common feature (e.g. age over x years, sex, medical condition) or symptom (e.g. high blood pressure) that all (or the majority) of the patients of the training data for which the result of the task-specific artificial neural network is known have, or are supposed to have, according to the current state of medicine.

The domain-specific artificial neural network may also be used during inference, e.g. for a physician using the system according to invention to double-check the results of the task-specific artificial neural network.

In some advantageous embodiments, the cost function comprises a term that penalizes parameters of at least a sub-set of parameters of the artificial neural network structure for being non-zero. Parameter in this context may mean any value that may be adjusted during, and as a result of, the training of the artificial neural network structure. Parameters may therefore include weights, biases and/or values of the weighting factors of the weighting gate modules. In order to fine-tune this balance, the term penalizing non-zero entries may be weighted with a manually settable hyperparameter.

Penalizing non-zero parameters is one way to decrease the number of non-zero entries of the intermediate and final outputs of the artificial neural network structure by setting less relevant parameters to zero, thus generally making computation easier and faster. In general, highly relevant parameters will not be set to zero despite the term because the benefits of the highly relevant parameters having specific non-zero values will outweigh the penalties.

In some advantageous embodiments, the artificial neural network structure has been trained using training data comprising triplets consisting of a corresponding anchor dataset, neighbor dataset and impostor dataset. The cost function may comprise a term based on a difference between the anchor dataset and the neighbor dataset as well as on a difference between the anchor dataset and the impostor dataset. The differences may be determined, (e.g. distances may be calculated) in a space of the medical data structure, for example using a Hamming distance metric, after being binarized, an L1 or an L2 distance metric. Using such triplets for training helps to bias the system towards known medical correlations which are represented by the "neighbors" and away from irrelevant, or incorrect, correlations which are represented by the "impostors".

In some advantageous embodiments, the system comprises a data storage for storing a plurality of medical data structures of a plurality of patients, for example a computer memory, a solid-state disc memory and/or the like. The data storage may be realized as a local device, e.g. integrated in, or sharing a housing with the computing device. The data storage may also be a remote or distributed data storage such as a cloud-based memory.

In some advantageous embodiments, the system comprises a search module configured to compare the medical data structure for a patient to be diagnosed with a plurality of other medical data structures stored in the data storage, and to retrieve a cohort of patients similar to the specific patient based on a similarity metric between the respective medical data structures. The similarity metric may e.g. be Hamming distance, an L1 or an L2 distance metric. Since the medical data structures are generated such as to maximize their relevant data content, similarities of the medical data structures indicate similarities in medically relevant data, as opposed to similarities that may seem relevant (e.g. same age) but that might not be relevant in certain circumstances.

In particular when the medical data structure is task-specific (i.e. generated using an artificial neural network structure that has been trained including the task-specific artificial neural network), and preferably also domain-specific (i.e. generated using an artificial neural network structure that has been trained as including the domain-specific artificial neural network), the similarity between medical data structures will translate to a task-specific and domain-specific similarity of medical data of the respective patients. Such similarities may uncover new correlations between patients with different symptoms and/or diseases.

In some advantageous embodiments, the system comprises an analysis module configured to perform an analysis of the cohort of patients retrieved by the search module and to generate a graphical representation of medical information for the patient to be diagnosed based on results of the analysis.

In some advantageous embodiments, the data storage and/or the search module and/or the analysis module are implemented by a remote device of the system according to the first embodiment and/or a cloud computing system that is part of the system according to the first embodiment. In this way, resource- and/or computing-power-intensive algorithms, or parts of algorithms may be performed, or modules executed, on an especially powerful and/or particularly suited platform.

In some advantageous embodiments, the medical data structure consists of a matrix (preferably of a vector) and all entries of the matrix have values in the range from zero to one, including both zero and one. This simplifies many distance metrics and other comparisons.

FIG. 1 shows a schematic diagram illustrating a system 1000 for providing a medical data structure 200 for a patient 1. The medical data structure 200 may also be designated as a "compact signature" or a "digital medical fingerprint" of the patient 1 and is therefore depicted as a stylized fingerprint, alluding to the personal nature of the data.

The system 1000 comprises a plurality of data sources 11-1, 11-2, 11-3, 11-4, 11-5, 11-6 (collectively designated as 11-i), each providing medical data of the patient 1. The data sources 11-i may each belong to a different modality.

As illustrated in FIG. 1, the data sources 11-i may, for example, comprise ultrasound imaging data 11-1, tomography imaging data 11-2, lab result data 11-3, 11-5, genetic data 11-4 and/or questionnaire data 11-6. The data sources 11-i consist of, or comprise, data storage sections in a data storage unit of the system 1000 and/or in a cloud computing system. Some or all of the data sources 11-i may be realized as comprising, or consisting of, interfaces (comprising hardware and/or software components) that provide the medical data of the patient 1 from outside of the system 1000.

The system 1000 further comprises a computing device 100 configured to implement a trained artificial neural network structure 10 comprising a plurality of trained neural networks (or: "sub-networks").

The artificial neural network structure 10 comprises a plurality of encoding modules 12-1, 12-2, 12-3, 12-4, 12-5, 12-6 (collectively designated as 12-i), wherein for each data source 11-i at least one, preferably exactly one, encoding module 12-i is provided. The encoding modules 12-i are each realized as an artificial neural network configured and trained to generate, from the medical data from the corresponding data source 11-i, a corresponding output matrix (e.g. an output vector or an output scalar), indicating medical information about the patient 1. As a result from the encoding modules 12-i, the output matrix may be designated as an "encoded output matrix".

The encoded output matrices of the encoding modules 12-i are preferably of a lower dimension than the underlying medical information about the patient 1 on which the respective encoded output matrix is based. Preferably, the encoding modules 12-i comprise, or consist of, de-noising autoencoders, for example as described in Miotto et al. De-noising autoencoders can help to "fill in" information missing in the medical information and/or to reduce, or condense, the medical data to fewer, more relevant data items.

The artificial neural network structure 10 further comprises a weighting gate module 14-1, 14-2, 14-3, 14-4, 14-5, 14-6 (collectively designated as 14-i) for each of the encoding modules 12-i, each weighting gate module 14-i configured to weight the encoded output matrix of the corresponding encoding module 12-i by multiplying it with a weighting factor $\alpha_i$ within a predetermined weighting range, preferably between 0 and 1, including both. In some embodiments, the weighting factors $\alpha_i$ are set by an operator; however, in preferred embodiments, the weighting factors $\alpha_i$ are parameters that are learned during training of the artificial neural network structure 10, as will be described in the following in more detail.

The artificial neural network structure 10 further includes a concatenation module 16 configured to concatenate the weighted output matrices of the weighting gate modules 14-i to a "concatenated encoded output matrix". When all of the output matrices are vectors ("output vectors"), then the concatenated output matrix is a concatenated output vector.

The artificial neural network structure 10 also comprises an aggregation module 18 realized as an artificial neural network configured and trained to receive the concatenated output matrix and to generate therefrom the medical data structure 200 for the patient 1, for example as described in EP 3 223 183 A1, the entire contents of which are hereby incorporated herein by reference.

Advantageously, the artificial neural network structure 10 is trained using a single cost function E, advantageous variations of which will be described in the following with respect to FIG. 2. Incidentally, a method of training an artificial neuronal network structure 10 according to the sixth embodiment of the invention is described.

Figure 2:
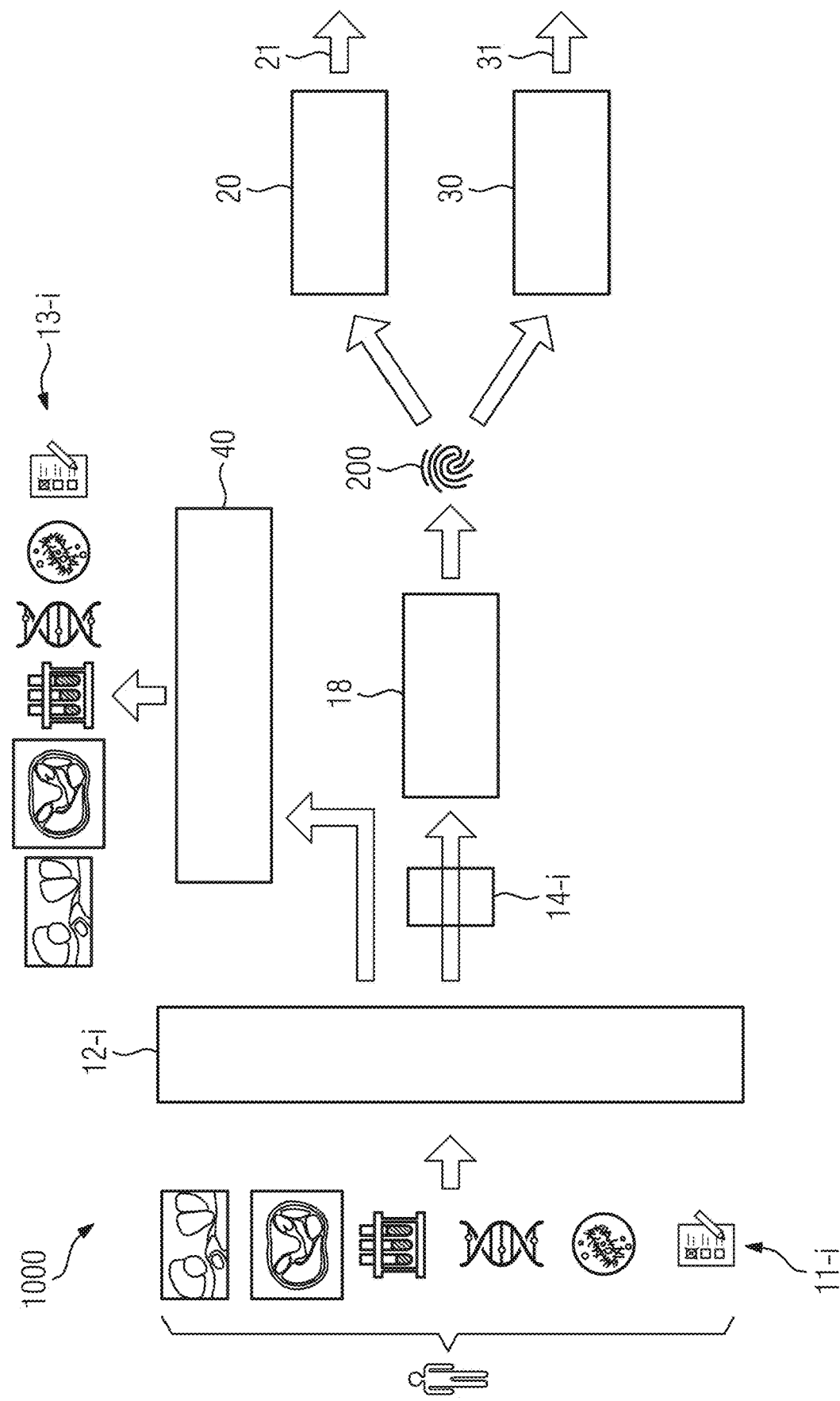
FIG. 2 shows a schematic diagram illustrating a system according to another embodiment of the present invention.

FIG. 2 schematically shows the artificial neural network structure 10 including further artificial neural networks and/or modules that are advantageous for training the artificial neural network structure 10 but which may also be used during the inference stage, i.e. during use of the system 1000 by an operator.

Advantageously, at least for the purpose of training, but optionally also during use, the artificial neural network structure 10 comprises a task-specific artificial neural network 20 (or: "task-specific sub-network") configured and trained to perform, using the medical data structure 200 as an input, a diagnostic and/or prediction task for the patient 1 and to output a task output matrix 21 indicating a result of the diagnostic and/or prediction task.

The output task matrix 21 is advantageously a scalar with a target set of discrete values, for example binary values of "0" and "1". For example, in the context of cardiovascular disease, the task output matrix could be a numerical value indicating the risk of having myocardial infarction within the next three years. A "0" may indicate "no risk present" and a "1" may indicate "risk present".

The cost function E used for training the artificial neural network structure 10 using training data is preferably designed such as to penalize differences between the task output matrices 21 for the training data and corresponding labels of the training data. In the case of a scalar as the task output matrix 21, the cost function E may be based on a difference between that value and the corresponding labels of the training data.

In the specific case that the task output matrix 21 is a scalar with binary values of "0" and "1" (e.g. the output of a binary classification network), the cost function E may specifically comprise a binary cross-entropy term as loss contribution $E_{task}$ from the task-specific artificial neural network 20, for example:

$$E_{task} = \Sigma_n (y_n \cdot \log(\bar{y}_n) + (1 - y_n) \cdot \log(1 - \bar{y}_n)),$$

wherein the sum indicated by "$\Sigma_n$" runs over all "n", wherein the $\bar{y}_n$ denote the outputs (a scalar, or any or all individual entries of a task output matrix 21) of the task-specific artificial neural network 20 based on the training data and wherein the $y_n$ denote the corresponding ground truth labels (e.g. "1" or "0", or, equivalently, "at risk" or "not at risk" and the like).

In the above example, training data could comprise medical data from patients that are labelled with a zero ("no risk present") when, within three months after the time where the medical data of the training set were provided, the corresponding patient did not have myocardial infarction, and labelled with a one ("risk present") when, within the three months, the corresponding did have myocardial infarction.

By training the artificial neural network structure 10 in this way, it is ensured that the medical data structure 200 is generated in such a way that is does not lose its diagnostic/predictive value for the task at hand. In that sense, the medical data structure 200 trained using a cost function E comprising a loss contribution from the task-specific artificial neural network 20 may also be designated as a task-specific medical data structure 200.

Apart from training, the task-specific artificial neural network 20 may also be used during an inference stage, i.e. when the same task is to be performed for the patient 1 to be diagnosed.

When more than one task is to be performed for a given patient, it may be advantageous to have one task-specific medical data structure 200 for each task. Accordingly, the system 1000 may comprise a plurality of artificial neural network structures 10 for the same patient 1, each being trained to be task-specific to a different diagnostic and/or predictive task.

As an alternative, one artificial neural network structure 10 may comprise a plurality of task-specific artificial neural networks 20 that are trained together with the single cost function E and each of which contributes its own cost contribution to it.

The system 1000 may comprise a domain-specific artificial neural network 30 configured and trained to determine, using the medical data structure 200 as an input, a medical domain for the patient and for the diagnostic and/or prediction task and to output a domain output matrix 31 indicating the determined medical domain. The domain output matrix 31 may be a vector or even a scalar, e.g. a scalar having a target set of discrete value, in particular a binary target set.

In the above example regarding the task of predicting a risk of myocardial infarction within three months, the medical domain may e.g. be characterized by a binary scalar, wherein a value of "1" indicates "patient has high blood pressure" and a value of "0" indicates "patient does not have high blood pressure", for a given threshold of blood pressure values.

The cost function E used for training the artificial neural network structure 10 comprises a term $E_{domain}$ that penalizes differences between the domain output matrices for the training data and corresponding labels of the training data.

In a case where the domain output matrix 31 is a binary scalar value (e.g. "1" and "0" representing two mutually exclusive facts), $E_{domain}$ may comprise, or consist of, a binary cross-entropy term as has been described in the foregoing with respect to $E_{task}$. If the domain output matrix 31 is a vector or a matrix of at least two rows and two lines with binary entries, $E_{domain}$ may comprise, or consist of, a binary cross-entropy term for each entry of the domain output matrix 31.

For domain output matrices 31 that have entries with continuous values (for example a scalar with continuous values between 0 and 1, including both, or between minus infinity and plus infinity), other known cost function terms may be used such as mean squared error terms, square mean difference terms and/or the like.

For example, high blood pressure is known to increase the likelihood of myocardial infarction. When the task is to diagnose likelihood of myocardial infarction, the medical data structure 200 should be generated such that the domain-specific artificial neural network 30 will retrieve from it that the patient belongs to a group of patients exhibiting the symptom of high blood pressure, i.e. belongs to the domain of "having high blood pressure".

The domain-specific artificial neural network 30 may also be used during inference, e.g. for a physician using the system 1000 to double-check the results of the task-specific artificial neural network 20. This can be used to increase confidence of the physician and/or the patient in the results of the system 1000.

For example, suppose that the task-specific artificial neural network 20 were to generate, from the medical data structure 200 of the patient 1 that the patient 1 is at risk of having myocardial infarction within the next three months, and the domain-specific artificial neural network 30 were to generate, from the same medical data structure 200 of the patient 1, that the patient should have low blood pressure. In that case, the operator of the system 1000 (e.g. a physician) could infer that the task output matrix 21 could be less reliable than usual, because a) the operator might know that patients with a high risk of having myocardial infarction (almost) always have high blood pressure and/or b) because the operator might have measured the blood pressure of the patient 1 and found it to be high.

In other words, the operator (or a program code automatically performed by the computing device 100) may compare the domain output matrix 31 with a recent measurement or test result of the patient 1 and, when they match, credit the task output matrix (and/or results of other parts of the artificial neural network structure 10) with higher credibility than when they do not match.

Similarly, the domain output matrix 31 may indicate to the operator (e.g. physician) an additional test (in the present example, of the blood pressure of the patient 1) to be performed in order to corroborate the task output matrix.

The artificial neural network structure 10 preferably further comprises at least one decoding module 40, each decoding module 40 corresponding specifically to one of the encoding modules 12-$i$. Each decoding module 40 is preferably realized as an artificial neural network configured and trained to generate at least one piece of information 13-$i$ relating to the medical data from the data source 11-$i$ of the corresponding encoding module 12-$i$.

In other words, the decoding modules 40 verify that, during the encoding by the encoding modules 12-$i$ (preferably to a modality-specific, latent, low-dimensional space) predetermined relevant information is not lost.

The cost function E used for training the artificial neural network structure 10 may therefore advantageously comprise a term $E_{reconstruction}$ that penalizes differences between the generated pieces of information for the training data and corresponding labels of the training data and/or the medical data. The term $E_{reconstruction}$ may comprise a squared difference between at least one entry (or feature) of the original medical data $X_n^m$ and the corresponding reconstructed entry (or feature) $\dot{X}_n^m$ produced by the decoding module 40 from the encoded output matrix of the corresponding encoding module 12-$m$ for the data source 11-$m$. In this notation, $X_n^m$ denotes entry n of a vector representing medical data from data source 11-$m$, and $\dot{X}_n^m$ denotes the corresponding reconstructed entry. The entries $X_n^m$ may represent individual medical properties of the patient 1, e.g. an age, a heart rate at rest, a body-mass index (BMI) and the like.

In the event that for data source 11-$m$ all of the entries are to be reconstructed (i.e. when all entries of the data source 11-$m$ have been predetermined to be medically relevant for a task at hand), then the term $E_{reconstruction}$ may comprise, or consist of, a term $1/N \cdot \Sigma_n (\dot{X}_n^m - X_n^m)^2$, wherein N is the dimensionality (i.e. number of entries) of the vector $X^m$ or, in other words, the number of features of data source 11-$m$, and wherein $\Sigma_n$ denotes a sum running from n=1 . . . N. When only a sub-set of the entries of the vector $X^m$ has been predetermined to be medically relevant to the task at hand, the sum $\Sigma_n$ may be taken only over those entries, e.g. only over entries 1, 3, 4 and 7 out of N=10 entries.

Similarly, when all of the entries of all of the data sources 11-$i$ have been predetermined to be medically relevant for the task at hand, then the term $E_{reconstruction}$ may comprise, or consist of, a term $1/(NM) \cdot \Sigma_m \Sigma_n (\dot{X}_n^m - X_n^m)^2$, wherein $\Sigma_m$ is a sum over all data sources 11-$i$, i.e. from m=1 . . . M, M being the number of data sources 11-$i$ (i.e. M=6 in the example shown in FIG. 1 and FIG. 2), and $\Sigma_n$ is, again the sum over all entries of the vectors $X^m$.

It should be noted, however, that N may be a function of m as well, N=N(m), as different data sources 11-$i$ may have different dimensionality N, i.e. different lengths of vectors, or, in other words, different amounts of features. As has been discussed before, for example, medical imaging data may comprise dozens or hundreds of entries, each corresponding to a pixel (e.g. N(m=1)=100), whereas lab result data may have only a single entry (e.g. N(m=3)=1), e.g. a test for a specific substance being positive or negative.

Similarly, as has been described in the foregoing, both the sum over m and the sum over n do not have to include all M data sources 11-$i$ and/or all entries N(m) of each data source 11-$m$ but may include only selected data sources 11-$i$ and/or only selected entries of the vector representing the medical data from the respective data source 11-$i$.

As an example, when the questionnaire data as one data source 11-6 comprises medically highly relevant information such as preexisting conditions and medically less relevant information such as a level of healthcare insurance, the corresponding decoding module 40 for the data source 11-6 may be configured and trained to retrieve the information about the previously existing conditions from the encoded output matrix of the encoding module 12-6 for the data source 11-6.

When, as is preferred, the entire artificial neural network structure 10 is trained as a whole using the cost function E, this means that also the encoding module 12-6 is trained to encode the medical data from the data source 11-6 such that the predetermined relevant information (in the example the preexisting conditions) is retrievable by the corresponding decoding module 40. In this way, it is ensured that the predetermined relevant information from the data source 11-6 is encoded in the encoded output matrix so that it can influence the medical data structure 200.

For the sake of clarity, only one decoding module 40 is shown in FIG. 2. However, it should be understood that there may be provided one (or at least one) decoding module 40 for each encoding module 12-$i$. It is also possible to provide more than one decoding module 40 for at least one of the encoding modules 12-$i$, for example when more than one piece of information for the encoding module 12-$i$ has been determined.

The cost function E may further comprise a term R that penalizes parameters $\theta_i$ of at least a sub-set of parameters $\theta_i$ of the artificial neural network structure 10 for being non-zero. Such a term R may be designated as a "regularization term" and is used to keep the artificial neural network structure 10 from overfitting to a training set. For example, the term R may comprise, or consist of, a term proportional to $\|\theta\|_1$, wherein $\|\cdot\|_1$ denotes the classical L1 regularization of a vector, and wherein $\theta$ is a vector comprising parameters of the artificial neural network structure 10, preferably all parameters of the artificial neural network structure 10.

The total cost function E may, in a preferred embodiment, be defined as $$E = \lambda_1 \cdot E_{task} + \lambda_2 \cdot E_{domain} + \lambda_3 \cdot E_{reconstruction} + \lambda_4 \cdot R$$

with hyperparameters $\lambda_1$ to $\lambda_4$.

To optimize the cost function E, any known optimizer may be used, e.g. a stochastic gradient descent.

Optionally, the cost function E may in addition to the terms shown above, or replacing one or more of the terms above, comprise a so-called triplet loss term $E_{triplets}$.

Such a term is used when the artificial neural network structure 10 is trained with training data that comprise triplets consisting of a corresponding anchor dataset, neighbour dataset and impostor dataset. The term "neighbour dataset" refers to a dataset that is expected and desired to yield a result (in the present case, a medical data structure 200) comparatively similar to the "anchor dataset", and the term "impostor dataset" refers to a dataset that is expected and desired to yield a result comparatively less similar to the "anchor dataset". Specifically, the medical data structure 200 based on the "neighbour dataset" should be more similar to the "anchor dataset" than the "impostor dataset" is to the "anchor dataset".

This may be realized by the term $E_{triplets}$ comprising, or consisting of, a term proportional to $$1/K \, \Sigma_k [\|z_k^{anchor} - z_k^{neighbour}\|^2 - \|z_k^{anchor} - z_k^{impostor}\|^2 + \mu]_+,$$

wherein $z_k$ stands for the entries of the medical data structure 200 for a given patient 1, k running from 1 to K, K being the dimensionality of the medical data structure 200 (e.g. the length of a vector), $\Sigma_k$ is the sum over k from 1 to K, and $\mu$ is the target margin between similar samples and the impostor. The function $[[\cdot]]_+$ computes the maximum between zero and the term between the brackets. The term is large when the difference (in the space of the medical data structure 200) between the anchor dataset and the impostor dataset is smaller than the distance between the anchor dataset and its neighbour dataset.

Use of the triplet loss term $E_{triplets}$ is especially advantageous when important domain parameters (that may be modelled also in the domain output matrix) are known that would e.g. require two patients having similar conditions with respect to that domain parameter to also have similar medical data structures 200. In the above example of the task of determining the risk of myocardial infarction and a binary scalar domain output matrix indicating high blood pressure ("1") or low blood pressure ("0"), then the anchor dataset and the neighbour dataset could be of patients having high blood pressure whereas the impostor dataset could be of a patient having similar age, sex etc. but having low blood pressure.

Any or all of the above described steps for training the artificial neural network structure 10 may be performed. Accordingly, the present invention provides also a method for training an artificial neural network structure 10.

Figure 3:
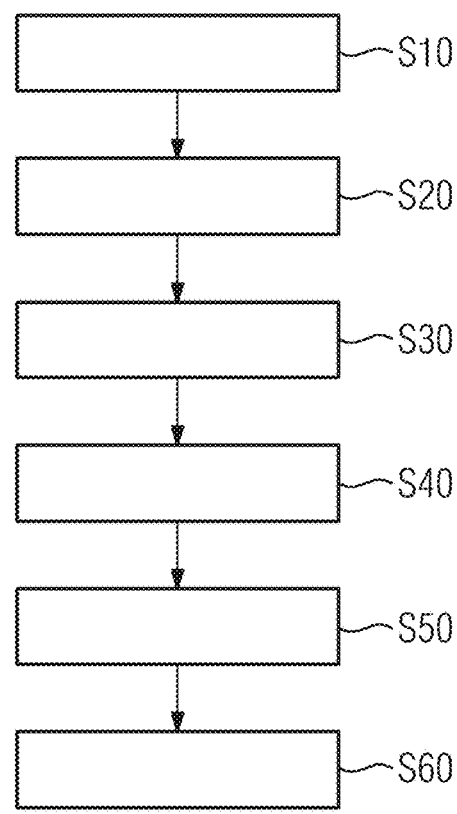
FIG. 3 shows a schematic flow diagram illustrating a method according to the second embodiment of the present invention.

FIG. 3 shows a schematic flow diagram illustrating a method for providing a medical data structure 200 for a patient 1 according to the second embodiment of the present invention. The method of FIG. 3 is usable with the system according to the first embodiment of the present invention, in particular with the system 1000 of FIG. 1 and/or FIG. 2. The method of FIG. 3 may therefore be provided with any options or variations that have been described with respect to the system according to the first embodiment and vice versa. Moreover, all of the details of the artificial neural network structure 10 described in the foregoing may equally apply to the method of FIG. 3.

In the following use will be made of some reference signs of FIG. 1 and/or FIG. 2 for better illustration of the method of FIG. 3.

In a step S10, medical data of the patient 1 from a plurality of data sources 11-$i$ are provided, e.g. as has been described in the foregoing with respect to data source interface, data storages and so on. In particular, medical data from a plurality of different data sources 11-$i$ (or: "modalities") may be provided.

In a step S20, a trained artificial neural network structure 10 is provided, the artificial neural network structure 10 comprising at least one encoding module 12-$i$ for each data source 11-$i$, in particular as has been described with respect to FIG. 1 and FIG. 2. Preferably, the artificial neural network structure 10 is trained, in its entirety, as has been described in the foregoing, especially with respect to the cost function E. In especially preferred embodiments, the artificial neural network structure 10 is trained using the task-specific artificial neural network 20 and/or the domain-specific artificial neural network 30 and/or the at least one decoding module 40.

In a step S30, a corresponding encoded output matrix is generated from the medical data of each data source 11-$i$ by a corresponding encoding module 12-$i$, in particular as has been described with respect to FIG. 1 and FIG. 2.

In a step S40, the encoded output matrices of the encoding modules 12-$i$ are weighted, by a corresponding weighting gate module 14-$i$, by multiplying each encoded output matrix with a weighting factor $\alpha i$, preferably within a predetermined weighting range between 0 and 1, both included, as has been described in the foregoing. The weighted encoded output matrices are also designated as "weighted output matrices" herein.

In a step S50, the weighted output matrices are concatenated to form a concatenated weighted encoded output matrix (or: "concatenated output matrix" for short).

In a step S60, the medical data structure 200 for the patient 1 is generated from the concatenated output matrix using an aggregation module 18 realized as a trained artificial neural network, in particular as has been described in the foregoing with respect to FIG. 1 and FIG. 2.

It has already been described in the foregoing how already the task-specific artificial neural network 20 and/or the domain-specific artificial neural network 30 may be used advantageously by an operator (e.g. a physician) to help with the diagnosis (i.e. diagnostic task) of the patient 1.

Further possible variants, features and applications of the system 1000 are described in the following with respect to FIG. 4 and FIG. 5. Since the system 1000 may also be used for diagnosing a patient 1, the system 1000 may, especially in the embodiment shown in FIG. 4, also be designated as a "medical support system" or as a "diagnostic system".

Figure 4:
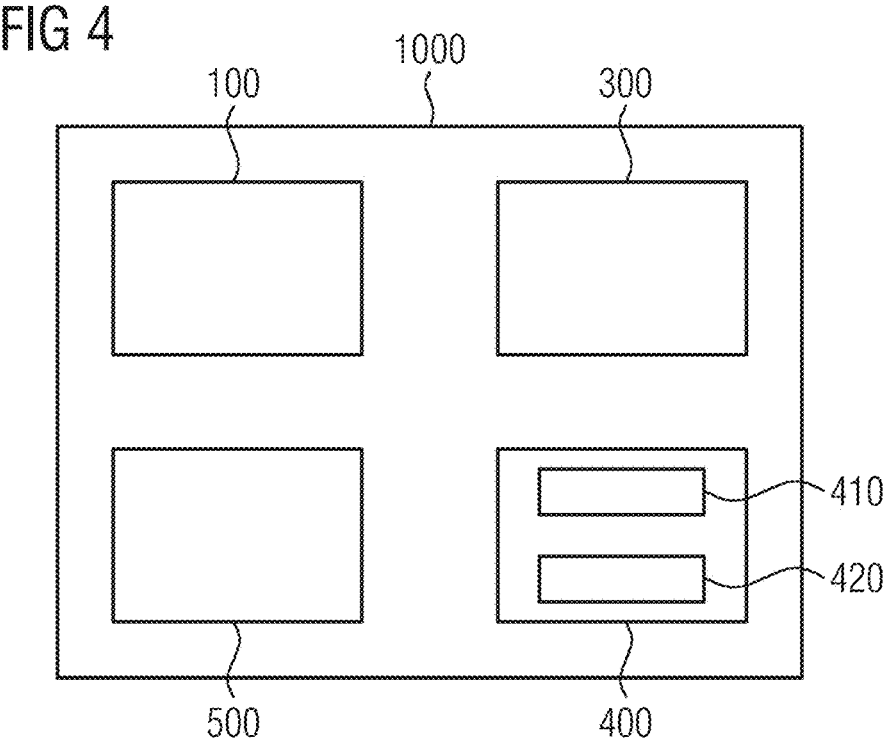
FIG. 4 shows a schematic block diagram illustrating a system according to yet another embodiment of the first embodiment of the invention.

FIG. 4 shows a schematic block diagram of another embodiment of the system according to the first embodiment, the system being a variant of the system according to FIG. 1 and/or FIG. 2.

Figure 5:
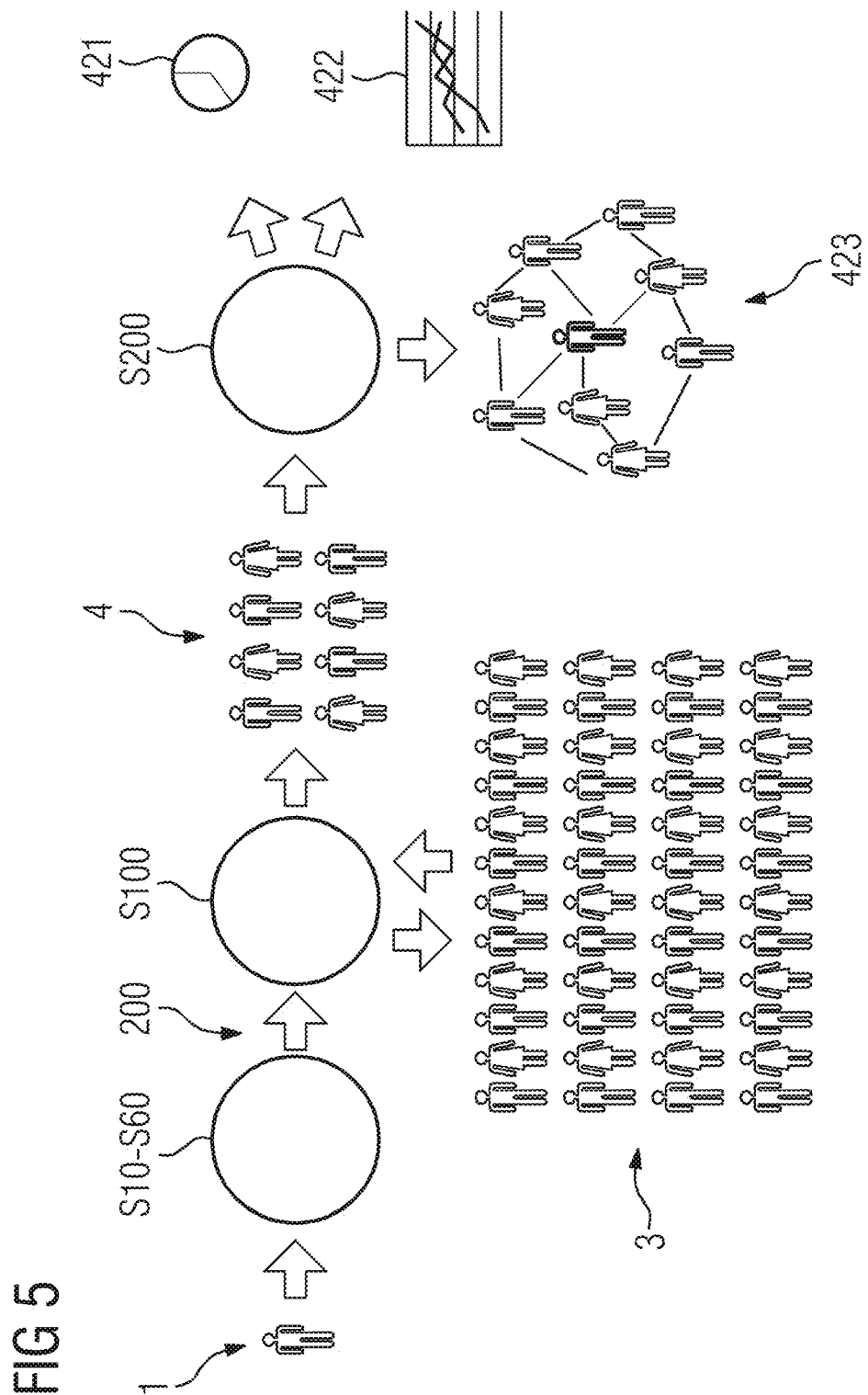
FIG. 5 shows a schematic flow diagram of a method according to another embodiment of the second embodiment.

FIG. 5 shows a schematic flow diagram of a method for providing information about a patient 1 to be diagnosed, which is a variant of the method according to the second embodiment of the invention.

Referring to FIG. 4, the system 1000 may further comprise a data storage 300 for storing a plurality of medical data structures 200 of a plurality of patients 1. The data storage 300 may be a local data storage, e.g. arranged in a housing that also comprises the computing device 100. Preferably, the data storage 300 has a distributed file system such as HDFS provided by Apache Hadoop. The data storage 300 may in some variants comprise any or all of the data sources 11-$i$.

When a new patient dataset of a new patient 1 is available, the medical data structure 200 for that patient 1 may be generated as has been described in the foregoing (e.g. steps S10-S60). This procedure is preferably performed locally (i.e. on a local computing device), for example within a hospital. In that way, the raw medical data of the patient 1 are especially well-protected.

After its generation, the medical data structure 200 may be sent to a cloud computing system 400, which may also be designated as a "cloud web-service component". The system 1000 comprises a search module 410 that is preferably implemented by the cloud computing system 400. The cloud computing system 400 may also comprise the data storage 300 (i.e. the data storage 300 may be a cloud data storage), wherein preferably a plurality of previously generated medical data structures 200 is stored. The "new" medical data structure 200 sent to the cloud computing system 400 for search/analysis/query may then be stored together with the other medical data structures 200. Optionally, the search module 410 could also be implemented locally by the computing device 100.

The medical data structure 200 is preferably sent using HTTPS. The medical data structure 200 may be generated (using the step S10-S60) on demand and be sent immediately. As an alternative, or in addition, the generated medical data structures 200 may be stored locally and may be sent to the cloud computing system 400, e.g. by HTTPS, when needed. For example, an operator (e.g. a physician) may use a graphical user interface (GUI), for instance a web interface connected to the cloud computing system 400, to select a patient of interest from a local database and to send that patient's medical data structure 200 to the cloud computing system 400.

Since the medical data structure 200 is an encoded data object, a high degree of privacy may be maintained when the raw (and unencoded) medical data are only present and processed locally (e.g. on a computer or a local computer intranet, for example in a hospital) and when only the encoded medical data structures 200 are sent to remote computing systems and/or cloud computing systems 400 that may have lower privacy standards.

The search module 410 is configured to compare (step S100 in FIG. 5), the medical data structure 200 for a patient 1 to be diagnosed with a plurality 3 of other medical data structures 200 in the data storage 300 and to retrieve (or: find) a cohort 4 of patients similar to the specific patient 1 based on a similarity metric between the respective medical data structures 200. The comparing, and the retrieving (S100) of the cohort 4, can be performed efficiently using parallelization, i.e. by employing a plurality of processing units, or threads, of the cloud computing system 400 (and/or of the computing device 100) in parallel. The use of the cloud computing system 400 is preferred since step S100 typically requires considerable computing resources.

Advantageously, the entries of the medical data structures 200 all have values between 0 and 1, both included. The similarity metric used for the medical data structures 200 may use classical distance metrics such as Hamming distance, L1 or L2 distance metrics. The similarity computation by the search module 410 may be made more efficient by adopting a map-reduce strategy. The similarity computation could also be parallelized which will lead faster results, especially in cases where a similarity between a large amount of medical data structures 200 has to be computed.

Referring again to FIG. 4, the system may further comprise an analysis module 420. Preferably, the analysis module 420 is implemented by the cloud computing system 400. Alternatively, the analysis module 420 may be implemented by a local device, e.g. by the computing device 100.

The analysis module 420 is configured to perform (step S200 in FIG. 5) an analysis of the cohort 4 of patients retrieved (or: found) by the search module 410 and to display medical information for the patient 1 to be diagnosed based on results of the analysis.

The analysis module 420 may perform any or all of the following functions as part of the analysis:

The analysis module 420 may be configured to derive a probability of the patient 1 to be diagnosed by looking at the ratio of similar patients (e.g. all patients within the cohort 4, or even a selection of the patients within the cohort 4 based on a further similarity metric) being at risked compared to all patients on file. The derived ratio may be graphically depicted by a display device 500 of the system 1000, e.g. in the form of a pie chart 421.

The analysis module 420 may be configured to compute average expected outcomes over time for the retrieved patients of the cohort 4 for at least one therapy option (preferably for a plurality of therapy options). The computed outcomes may e.g. be graphically depicted by the display device 500, for instance in the form of line plots 422 with confidence intervals.

The analysis module 420 may be configured to generate a Kaplan-Meier curve which may then be shown by the display device 500.

The analysis module 420 may be configured to compute a similarity matrix based on at least one similarity metric applied to a plurality of medical data structures 200 for different patients. A graphical representation of the patient 1 to be diagnosed with links to graphical representations of the other patients may be generated (and shown by the display device 500).

Using the data structure comprising the representation of the patient 1 to be diagnosed, the links, and the representations of the other patients, subgroups may be identified by the analysis module 420. For example, clustering algorithms may be used for identifying the subgroups (or: clusters), e.g. connected components labelling using thresholding. Other methods of clustering and/or classification may be used, e.g. neural networks, k-means, discriminant analysis, support vector machines and the like. The analysis module 420 may be configured to generate graphical representations 423 of the identified subgroups, or clusters, which may then be displayed by the display device 500.

The range of further applications and functions of the analysis module 420 is large, as the system 1000 may be used for (early) diagnosis, screening, decision support and/or therapy selection. Known clinical outcomes may be used to perform inference for new patients to be diagnosed. In this way, for example, a risk of developing a certain disease in a subsequent time period (e.g. three months, three years etc.) may be determined, and/or the outcome of different therapies depending on the patient's medical data structure may be predicted.

Figure 6:
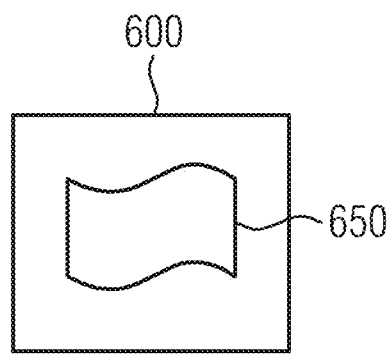
FIG. 6 schematically illustrates a computer program product according to the third embodiment of the invention.

FIG. 6 schematically illustrates a computer program product 600 comprising executable program code 650 configured to, when executed, perform the method according to the second embodiment of the present invention, in particular as has been described with respect to the previous figures.

Figure 7:
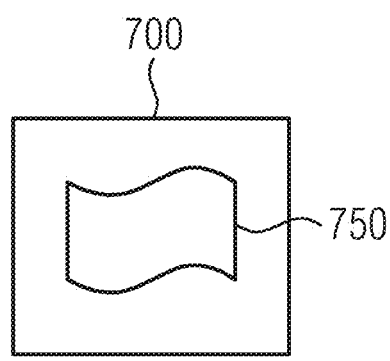
FIG. 7 schematically illustrates a non-transient computer-readable data storage medium according to the fourth embodiment of the invention.

FIG. 7 schematically illustrates a non-transient computer-readable data storage medium 700 comprising executable program code 750 configured to, when executed, perform the method according to the second embodiment of the present invention, in particular as has been described with respect to the previous figures.

Although specific embodiments have been illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for providing a medical data structure for a patient, the system comprising:
   a plurality of data sources, each data source of the plurality of data sources configured to provide medical data of the patient; and
   a computing device configured to implement an artificial neural network structure trained using a cost function, the artificial neural network structure including,
      a plurality of encoding modules, at least one of the plurality of encoding modules corresponding to each data source, each encoding module of the plurality of encoding modules being an artificial neural network configured and trained to generate, from the medical data from the corresponding data source of the plurality of data sources, a corresponding encoded output matrix,
      a plurality of weighting gate modules, each weighting gate module of the plurality of weighting gate modules corresponding with a respective encoding module of the plurality of encoding modules, each weighting gate module being configured to weight the encoded output matrix of the corresponding encoding module by multiplying the corresponding encoding module with a corresponding weighting factor, to produce a corresponding weighted output matrix, to produce weighted output matrices,
a concatenation module configured to generate a concatenated output matrix by concatenating the weighted output matrices to a concatenated corresponding output matrix, and
an aggregation module, the aggregation module being an artificial neural network, configured and trained to receive the concatenated output matrix and to generate, from the concatenated output matrix, the medical data structure for the patient.

2. The system of claim 1, wherein the weighting gate modules are configured to learn the weighting factors during training with the cost function.

3. The system of claim 2, wherein the artificial neural network structure includes a task-specific artificial neural network configured and trained to
perform, using the medical data structure as an input, at least one of a diagnostic task or a prediction task for the patient, and
output a task output matrix indicating a result of at least one of the diagnostic task or the prediction task, and
wherein the cost function is configured to penalize differences between the task output matrices for training data and corresponding labels of the training data.

4. The system of claim 3, wherein the artificial neural network structure includes a domain-specific artificial neural network configured and trained to
determine, using the medical data structure as an input, a medical domain for the patient and for at least one of the diagnostic task or the prediction task, and
output a domain output matrix indicating the medical domain,
wherein the cost function is configured to penalize differences between the domain output matrices for the training data and corresponding labels of the training data.

5. The system of claim 2, wherein the artificial neural network structure is trained using training data including triplets, the triplets including a corresponding anchor dataset, a neighbour dataset, and an impostor dataset, and
wherein the cost function includes a term based on
a difference between the corresponding anchor dataset and the neighbour dataset, and
a difference between the corresponding anchor dataset and the impostor dataset, the differences being determined in a space of the medical data structure.

6. The system of claim 2, further comprising:
a data storage configured to store a plurality of medical data structures of a plurality of patients; and
a search module configured to
compare the medical data structure for a patient to be diagnosed with a plurality of other medical data structures stored in the data storage, and
retrieve a plurality of patients similar to the patient based on a similarity metric between the medical data structures.

7. The system of claim 6, further comprising:
an analysis module configured to
perform an analysis of the plurality of patients, and
generate a graphical representation of medical information for the patient to be diagnosed based on results of the analysis.

8. The system of claim 7, further comprising:
at least one of a remote device or a cloud computing system, the at least one of the remote device or the cloud computing system configured to implement at least one of the data storage, the search module, or the analysis module.

9. The system of claim 7, further comprising:
at least one of a remote device or a cloud computing system, the at least one of the remote device or the cloud computing system configured to implement at least one of the data storage or the search module.

10. The system of claim 1, wherein the artificial neural network structure includes a task-specific artificial neural network configured and trained to
perform, using the medical data structure as an input, at least one of a diagnostic task or a prediction task for the patient, and
output a task output matrix indicating a result of at least one of the diagnostic task or the prediction task, and
wherein the cost function is configured to penalize differences between the task output matrices for training data and corresponding labels of the training data.

11. The system of claim 10, wherein the artificial neural network structure includes a domain-specific artificial neural network configured and trained to
determine, using the medical data structure as an input, a medical domain for the patient and for at least one of the diagnostic task or the prediction task, and
output a domain output matrix indicating the medical domain,
wherein the cost function is configured to penalize differences between the domain output matrices for the training data and corresponding labels of the training data.

12. The system of claim 1, wherein the artificial neural network structure includes at least one decoding module, each decoding module of the at least one decoding module corresponding to one of the encoding modules, each decoding module being an artificial neural network configured and trained to generate at least one piece of information relating to the medical data from the data source of the corresponding encoding module, and
wherein the cost function includes a term that penalizes differences between the generated pieces of information for training data and corresponding labels of at least one of the training data or the medical data.

13. The system of claim 1, wherein the cost function includes a term that penalizes parameters of at least a sub-set of parameters of the artificial neural network structure for being non-zero.

14. The system of claim 1, wherein the artificial neural network structure is trained using training data including triplets, the triplets including a corresponding anchor dataset, a neighbour dataset, and an impostor dataset, and
wherein the cost function includes a term based on
a difference between the corresponding anchor dataset and the neighbour dataset, and
a difference between the corresponding anchor dataset and the impostor dataset, the differences being determined in a space of the medical data structure.

15. The system of claim 1, further comprising:
a data storage configured to store a plurality of medical data structures of a plurality of patients; and
a search module configured to
compare the medical data structure for a patient to be diagnosed with a plurality of other medical data structures stored in the data storage, and retrieve a plurality of patients similar to the patient based on a similarity metric between the medical data structures.

16. The system of claim 15, further comprising:
an analysis module configured to
perform an analysis of the plurality of patients, and
generate a graphical representation of medical information for the patient to be diagnosed based on results of the analysis.

17. The system of claim 16, further comprising:
at least one of a remote device or a cloud computing system, the at least one of the remote device or the cloud computing system configured to implement at least one of the data storage, the search module, or the analysis module.

18. The system of claim 15, further comprising:
at least one of a remote device or a cloud computing system, the at least one of the remote device or the cloud computing system configured to implement at least one of the data storage or the search module.

19. The system of claim 1, wherein the medical data structure includes a matrix, all entries of the matrix including values in a range from zero to one, including both zero and one.

20. A method for providing a medical data structure for a patient, comprising:
providing medical data of the patient from a plurality of data sources;
providing a trained artificial neural network structure, the artificial neural network structure including a plurality of encoding modules, at least one of the plurality of encoding modules corresponding to each data source of the plurality of data sources;
generating, by the plurality of encoding modules, encoded output matrices based on corresponding medical data of each of the corresponding data sources;
producing weighted output matrices, by a plurality of weighting gate modules, by multiplying each of the encoded output matrices with a weighting factor, each weighting gate module of the plurality of weighting gate modules corresponding with one a respective encoding module of the plurality of encoding modules;
concatenating the weighted output matrices to a concatenated output matrix; and
generating the medical data structure for the patient from the concatenated output matrix using an aggregation module being a trained artificial neural network.

21. The method of claim 20, wherein the providing the trained artificial neural network structure includes training the artificial neural network structure using a cost function, the method further comprising:
performing, using the medical data structure as an input, at least one of a diagnostic task or a prediction task for the patient; and
outputting a task output matrix indicating a result of at least one of the diagnostic task or the prediction task,
wherein the cost function is configured to penalize differences between the task output matrices for training data and corresponding labels of the training data.

22. The method of claim 21, wherein the artificial neural network structure includes a domain-specific artificial neural network, the method further comprising:
determining, by the domain-specific artificial neural network, using the medical data structure as an input, a medical domain for the patient and for at least one of the diagnostic task or the prediction task; and
outputting, by the domain-specific artificial neural network, a domain output matrix indicating the medical domain,
wherein the cost function is configured to penalize differences between domain output matrices for the training data and corresponding labels of the training data.

23. The method of claim 22, wherein the cost function includes a term that penalizes parameters of at least a sub-set of parameters of the artificial neural network structure for being non-zero.

24. The method of claim 21, wherein the cost function includes a term that penalizes parameters of at least a sub-set of parameters of the artificial neural network structure for being non-zero.

* * * * *